US005947125A

United States Patent [19]
Benetti

[11] Patent Number: 5,947,125
[45] Date of Patent: Sep. 7, 1999

[54] METHOD FOR CORONARY ARTERY BYPASS

[75] Inventor: Frederico J. Benetti, Santa Fe, Argentina

[73] Assignee: Cardiothoracic Systems, Inc., Cupertino, Calif.

[21] Appl. No.: 08/889,616

[22] Filed: Jul. 7, 1997

Related U.S. Application Data

[63] Continuation of application No. 08/419,991, Apr. 10, 1995, Pat. No. 5,888,247.

[51] Int. Cl.$^6$ .................................................. A61B 19/00
[52] U.S. Cl. .............................................. 128/898
[58] Field of Search ......................... 623/1, 66; 128/898; 600/232; 606/193, 194, 195, 15, 159, 157

[56] References Cited

U.S. PATENT DOCUMENTS

| | | |
|---|---|---|
| Re. 34,150 | 12/1992 | Santilli et al. . |
| 4,726,356 | 2/1988 | Santilli et al. . |
| 4,852,552 | 8/1989 | Chaux . |
| 5,025,779 | 6/1991 | Bugge . |
| 5,429,144 | 7/1995 | Wilk . |
| 5,452,733 | 9/1995 | Sterman et al. . |

FOREIGN PATENT DOCUMENTS 2 267 827  12/1993  United Kingdom .

OTHER PUBLICATIONS

"Mammary Artery–Coronary Artery Anastomosis as Method of Treatment for Angia Pectoris," V.I. Kolessov, M.D.
*Thoracic and Cardiovascular Surgery*, vol. 54, No. 4, Oct., 1967, pp. 535–544.
"Direct Coronary Surgery with Saphenous Vein Bypass Without Either Cardiopulmonary Bypassor Cardia Arrest," F.J. Benetti.

*The Journal of Cardiovascular Surgery*, vol. 26, No. 3, May–Jun., 1985, pp. 217–222.
"Direct Myocardial Revascularization Without Cardiopulmonary Bypass," E. Buffolo; J.C.S. Andrade; J.Succi; L.E.V. Leao, and C. Gallucci.
*Thoac. Cardiovasc. Surgeon*, 33 (1985) pp. 26–29.
"Coronary Artery Revascularization Without Cardiopulmonary Bypass," R. Archer, D.O.; D.A. Ott, M.D.; R. Parravicini, M.D.; D.A. Cooley, M.D.; G.J. Ruel, M.D.; O.H. Frazier, M.D.; J.M. Duncan, M.D.; J.J. Livesay, M.D. and W.E. Walker, M.D.

(List continued on next page.)

*Primary Examiner*—David J. Isabella
*Attorney, Agent, or Firm*—Lyon & Lyon LLP

[57] ABSTRACT

The invention comprises a method for performing a coronary artery bypass graft on a beating heart under thoracoscopic visualization without opening the chest wall. At least one small opening is formed in the patient's chest, a target artery for an arterial blood supply is located, instruments are introduced through one or more small openings formed in the patient's chest to prepare the target artery for fluid connection to the coronary artery, and instruments are introduced through one or more small openings formed in the patient's chest to connect the target artery to the coronary artery distal from a stenosis. In a preferred embodiment, a minimal left anterior intercostal thoracotomy provides access to form an anastomosis between the left internal mammary artery (LIMA) and the left anterior descending artery (LAD) while thoracoscopic viewing facilitates harvesting the LIMA. In other embodiments, access to the patient's heart may be obtained through a trocar sheath or other means for providing percutaneous access to the patient's thoracic cavity without opening the chest wall. Thoracoscopic visualization, depending on the procedure, is used to locate the arterial blood supply, the location of the coronary artery to be bypassed and the location of the occlusion in the artery. In other embodiments, the diagonal (Dx) or circumflex (Cx) arteries may be bypassed.

10 Claims, 8 Drawing Sheets

OTHER PUBLICATIONS

*Texas Heart Institute Journal,* vol. 11, No. 1, Mar. 1984, pp. 52–57.
"Direct Myocardial Revascularization Without Extracorporeal Circulation," F.J. Benetti, M.D.; G. Naselli, M.D.; M. Wood, M.D.; and L. Geffner, M.D.
*Chest,* vol. 100, No. 2, Aug., 1991, pp. 312–316.
"Reoperative Coronary Artery Bypass Grafting Without Cardiopulmonary Bypass," W.J. Fanning, MD; G.S. Kakos, MD; and T.E. WIlliams, Jr., MD, PhD.
*The Annals of Thoracic Surgery,* vol. 55, No. 2, Feb. 1993, jpp. 486–489.
"Coronary Artery Bypass Without Cardiopulmonary Bypass," A.J. Pfister, MD; M.S. Zaki, MD; J.M. Garcia, MD; L.A. Mispireta, MD; P.J. Corso, MD; A.G. Qazi, MD; S.W. Boyce, MD; T.R. Coughlin, Jr., MD; and P. Gurny, MD.
*The Annals of Thoracic Surgery,* vol. 54, No. 6, Dec. 1992, pp. 1085–1092.
"To Use of Not To Use the Pump Oxygenator in Coronary Bypass Operations," Drs. W. G. Trapp and R. Bisarya.
*The Annals of Thoracic Surgery,* vol. 19, No. 1, Jan., 1975, pp. 108–109.
"Directed Myocardial Revascularization by Saphenous Vein Graft," R.G. Favaloro, M.D.; D.B. Effler, M.D.; L.K. Groves, M.D.; W.G. Sheldon, M.D.; and F.M. Sones, Jr., M.D.
*The Annals of Thoracic Surgery,* vol. 10, No. 2, Aug., 1970, pp. 97–111.
"Preservation of Interventricular Septal Function in Patients Having Coronary Artery Bypass Grafts Without Cardiopulmonary Bypass," C.W. Atkins, M.D.; C.A. Boucher, M.D.; and G.M. Pohost, M.D.
*American Heart Journal,* vol. 107, No. 2, Feb., 1984, pp. 304–309.
"Left Thoracotomy Reoperation for Coronary Artery Disease," Grosner, G, Lajos TZ, Schimertz G, Bergsland J.
*Journal of Cardiac Surgery,* 1990, vol. 5, pp. 304–308.
"Left Thoracotomy for Reoperation for Coronary Revascularation," Faro RS, Javid H, Najafi H., C. Serry.
*The Journal of Thoracic and Cardiovascular Surgery,* 1982, vol. 84, pp. 453–455.
"An Alternative Approach to Isolated Circumflex Coronary Bypas Reoperations," Cheung, D, Flemma RJ, Mullen DC, Lepley D, Jr.
*The Annals of Thoracic Surgery,* 1982, vol. 33, pp. 302–303.
"Left Thoracotomy for Reoperative Coronary Bypass," Burlingame, MW, Bonchek, LI, and Vazales, BE.
*Journal of Thoracic Cardiovascular Surgery,* 1988, vol. 95, pp. 508–510.
"Left Thoracotomy for Reoperative Coronary Artery Bypass Procedures," Ungerleider, RM, Mills NL, Wechsler, AS.
*The Annals of Thoracic Surgery,* 1985, vol. 40, pp. 11–15.
"Leftsided Thoracotomy for Coronary Artery Reoperation," Borst HG.
"Avoidance of Patent Anterior Grafts at Revisional Coronary Artery Surgery: Use of a Lateral Thoracotomy Approach," Walker, WS, Sang, CTM.
*Thorax,* 1986, vol. 41, pp. 692–695.

"Left Thoracotomy Approach for Coronary Artery Bypass Grafting in Patients with Pericardial Adhesions," Gandjbakheh I, Acar C, and Cabrol C.
*The Annals of Thoracic Surgery,* 1989, vol. 48, pp. 871–873.
"Right Thoracotomy for Reoperative Right Coronary Artery Bypass Procedures," Uppal, R, Wolfe, WG, Lowe JE, and Smith PK.
*The Annals of Thoracic Surgery,* 1994, vol. 57, pp. 123–125.
"Reoperation for Stenotic Saphenous Vein Bypass Grafts Without Cardiopulmonary Bypass," Akins CA.
*The Annals of Thoracic Surgery,* 1983, vol. 35, No. 2, pp. 201–206.
"Cardiopulmonary Bypass and Coronary Artery Bypass Graft," Corso PG.
*Chest,* 1991, vol. 100.
"Coronary Artery Bypass Without Cardiopulmonary Bypass—the Pros and the Cons," Moshkovitz Y. and Mohr R.
*Isr J Med Sci,* 1993, vol. 29, pp. 716–720.
"Minimally Invasive Coronary Artery Bypass Grafting: A New Method Using an Anterior Mediastinotomy," MC Robinson, DR Gross, W Zeman, and E Stedje–Larsen.
*Journal of Cardiac Surgery,* 1995, vol. 10, pp. 529–536.
"Coronary Artery Surgery Without Cardiopulmonary Bypass: Usefulness of the Surgical Blower–Humidifier," Maddaus M, Ali I, Birnbaum P, Panos AL, and Salerno TA.
*Journal of Cardiac Surgery,* 1992, vol. 7, No. 4.
"Technical Considerations for Coronary Artery Bypass Without Cardioplegia," Bonchek LI.
*Journal of Cardiac Surgery,* 1992, vol. 7, No. 4, pp. 333–341.
"Coronary Artery Bypass Grafting Without Cardiopulmonary Bypass," Arsiwala, S. Bedi HS, Sharma VK, and Trehan N.
*Indian Heart Journal,* 1990, vol. 42, No. 6, pp. 453–454.
"Right Anterolateral Thoracotomy for Repair of Atrial Septal Defect," Grinda JM, Folliguet TA, Dervanian P, Mace L, Legault B, Neveux JY.
*Ann Thorac Surg* 1996, vol. 62, pp. 175–178.
"Vertical Axillary Thoracotomy: A Functional and Cosmetically Appealing Incision," Baeza OR and Foster ED.
*The Annals of Thoracic Surgery,* 1976, vol. 22, No. 3, pp. 287–288.
"Transaxillary Minithoracotomy: The Optimal Approach for Certain Pulmonary and Mediastinal Lesions," Becker RM and Munro DD.
*The Annals of Thoracic Surgery,* 1976, vol. 22, No. 3, pp. 254–259.
"Simplified Lateral Chest Incision for Most Thoracotomies Other Than Sternotomy," Mitchell R, Angell W, Wuerflein R, and Dor V.
*The Annals of Thoracic Surgery,* 1976, vol. 22, No. 3, pp. 284–286.
"Coronary Artery Bypass Without Extracorporeal Circulation Versus Percutaneous Transluminal Coronary Angioplasty: Comparison of Costs," Benetti FJ.
*The Journal of Thoracic and Cardiovascular Surgery,* 1991, vol. 102, No. 5, pp. 802–803.
"Bypass Senza Spargimento di Sangue," Allori L.
*Salve,* 1995, N. 2, po. 38–42.
"Coronary Artery Bypass Grafting Surgery Without Cardiopulmonary Bypass," Kyobu N, Zasshi GG. (English Abstract Only Attached).

Department of Thoracic and Cardiovascular Surgery, St. Mary's Hospital, Kurme, Japan, 1993, vol. 4(4), pp. 598–602.

"A Case of Treating Abrupt Closure Due to Post PTCA Dissection by Emergent CABG–Reoperation, Via Extracorporeal Ciruclatory Method Conducted with the Heart 'Beating'," Kawase Y, Tanake, N, Mukai K, Matsumoto Y, Kawasuji M, and Watanabe Y. (English Abstract Only Attached).

*Japanese Journal of Thoracic Surgery,* 1993, vol. 46(6), pp. 512–515.

"Two–Staged Repeat Myocardial Revascularization Through the Sternal Re–Entry and the Left Thoracotomy with Coronary Anastomosis Under the Beating Heart," Horii T, Suma H, Wanibuchi Y, Fukuda, S, Kigawa I. (English Abstract Only Attached).

*Journal of the Japanese Association for Thoracic Surgery,* 1993, vol. 41(9), pp. 1511–1514.

"Current Status of Cardiac Surgery: A 40–Year Review," W.E. Richenbacher, MD; J.L. Myers, MD, FACC; J.A. Waldhausen, MD, FACC.

*Journal of the American College of Cardiology,* vol. 14, No. 3, Sep. 1989, pp. 535–544.

"The Impact of Additional Procedures on the Cost at Three Years of Coronary Angioplasty and Cornoary Surgery in the EAST Trial," WS Weintraub, PD Mauldin, E Becker, and SB King III.

*Circulation,* vol. 90, No. 4, Part 2, Oct. 1994, p. I–91.

"Closed–Chest Coronary Artery Bypass with Cardioplegic Arrest in the Dog," JH Stevens, LC Siegel, RS Mitchell, TA Burdon, GH Ribakove, JA SMith, FG St. Goar, WS Peters, MA Vierra, MF Pompili, and BA Reitz.

*Circulation,* vol. 90, No. 4, Part 2, Oct. 1994, p. I–251.

"Placement of Coronary Artery Bypass Graft Without Pump Oxygenator," WG. Trapp and R Bisarya.

*The Annals of thoracic Surgery,* (Jan. 1975) vol. 19, No. 1, pp. 1–9.

"Coronary Artery Bypass Surgery," BW. Lytle and DM Cosgrove III.

*Current Problems in Surgery,* (Oct. 1992), vol. XXIX, No. 10, pp. 737–807.

"Minimally Invasive Coronary Artery Bypass Grafting," TE Acuff, RJ Landreneau, BP Griffith, and MJ Mack.

*Ann Thorac Surg* (1996), vol. 61, pp. 135–137.

"Minimally Invasive Cardiopulmonary Bypass with Cardioplegic Arrest: A Closed Chest Technique with Equivalent Myocardial Protection," DS Schwartz; GH Ribakove, EA Grossi, JH Stevens, LC Siegel, FG St. Goar, WS Peters, D McLoughlin, FG Baumann, SB Colvin, and AC Galloway.

*The Journal of Thoracic and Cardiovascular Surgery,* (1996) vol. 111, No. 3.

"Coronary Surgery Without Cardiopulmonary Bypass," S Westaby.

*The Heart Journal,* (Mar. 1995).

Coronary Revasculariztaion with Arterial Conduits Via A Small Thoracotomy and Assisted by Thoracoscopy, Although Without Cardiopulmonary Bypass, FJ Benetti and C. Ballester.

*Cor Europaeum,* (1995) vol. 4(1), pp. 22–24.

"Controversies in Myocardial Revascularization: Coronary Artery Surgery for Single–Vessel Disease," CW Akins.

*Seminars in Thoracic and Cardiovascular Surgery,* (Apr. 1994) vol. 6, No. 2, pp. 109–115.

"A Minimally Invasive Surgical Method for Coronary Revascularization—Preliminary Experience in Five Patients," MC Robinson, DR Gross, and W Zeman.

*Circulation,* (Oct. 15, 1995) vol. 92, No. 8, I–176.

"Regional Cardiac Wall Immunobilization for Open Chest and Closed Heart Coronary Artery Bypass Grafting on the Beating Heart: The 'Octopus' Method, " C Borst, EWL Jansen, PF Grundemann, JWF van Dongen, HJ Mansvel Beck, H. Wesenhagen, PJ Slootweg, JJ Bredee.

*Circulation,* (Oct. 15, 1995) vol. 92, No. 8 supplement I, I–177.

"Influence of the Internal–Mammary–Artery Graft on 10–Year Survival and Other Cardiac Events," FD Loop, B.W. Lytle, DMCosgrove, et al.

*N. Eng. J. Med.,* 1986, vol. 3145, No. 1, pp. 1–6.

"Composite Arterial Conduits for a Wider Arterial Myocardial Revascularization," AM Calafiore, GD Giammarco, N. Luciani, et al.

*Ann. Thorac. Surg.,* 1994, vol. 58, pp. 185–190.

"Total Revascularization with T Grafts," AJ Tector, S Amundsen, TM Schmahl, et al.

*Ann. Thorac. Surg.,* 1994, vol. 57, pp. 33–39.

"Anastomosis Mamariocoronaria Sin Circulation Exracorporea," FJ Bennetti, J Rizzardi, R Aun, et al.

*Prense Medica Argen.* 1986, vol. 73, pp. 213–215.

"A New Internal Mammary Artery Retractor," M. Bugge.

*Thorac. Cardiovasc. Surgeon,* vol. 38, 1990, pp. 316–317.

"Internal Mammary Retractor,"RA Beg, H. Naraghipour, EB Kay and P Rullo.

*The Annals of Thoracic Surgery,* vol. 38, No. 1, Jan. 1985, pp. 286–287.

"A New Concept in Sternal Retraction: Applications for Internal Mammary Artery Dissection and Valve Replacement Surgery," A Chaux and C Blanche.

*Ann. Thorac. Surg.,* vol. 42, Oct. 1986, pp. 473–474.

"A Compact Single Post Internal Mammary Artery Dissection Retractor," JG Vincent.

*Eur. J. Cardiothorac Surg.,* 1989, vol. 3, pp. 276–277.

"A Modified Sternal Retractor," N Ancalmo and Jl Ochsner.

*The Annals of Thoraic Surgery,* vol. 21, Jan.–Jun. 1976, p. 174.

"A Modified Sternal Retractor for Exposure of the Internal Mammary Artery," PP McKeown, J Crew, Es Hanna, and R Jones.

*The Annals of Thoracic Surgery,* vol. 32, Jan./Jun. 1976, p. 619.

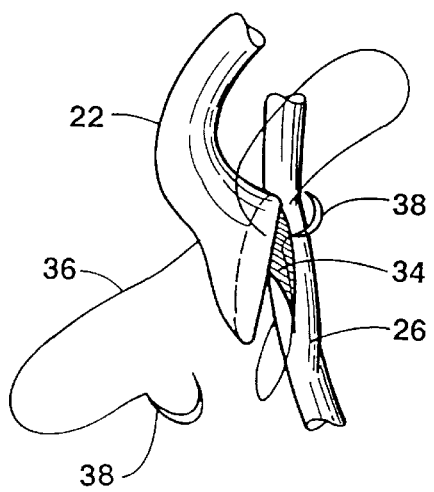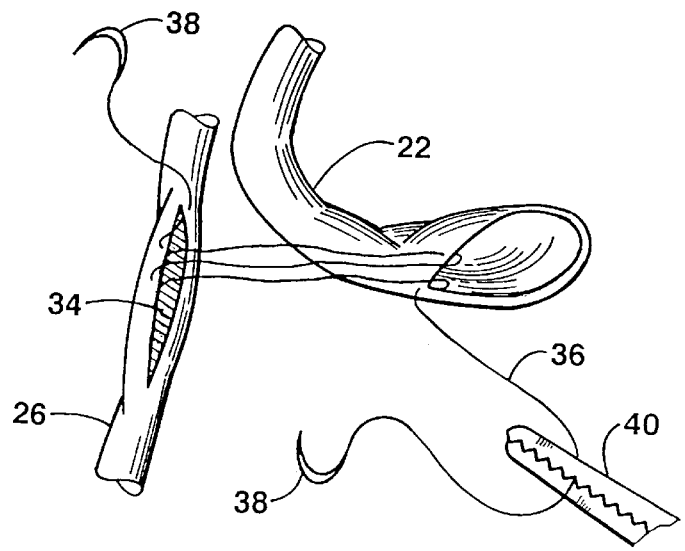
Fig.6
Fig.7
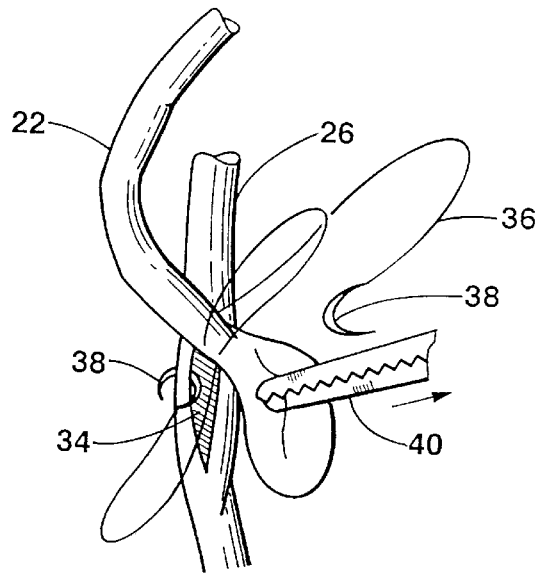
Fig.8

METHOD FOR CORONARY ARTERY BYPASS

This is a continuation of application Ser. No. 08/419,991, filed Apr. 10, 1995, now U.S. Pat. No. 5,888,247, and the above-identified application is expressly incorporated herein by reference.

BACKGROUND OF THE INVENTION

This invention is directed to a method for performing a minimally invasive coronary artery bypass graft. More particularly, the method permits a thoracoscopic procedure without the need for extracorporeal circulation or other cardiopulmonary bypass.

A coronary artery bypass graft (CABG) involves performing an anastomosis on a diseased coronary artery to reestablish blood flow to an ischemic portion of the heart muscle. Improved long-term survival has been demonstrated bypassing the left anterior descending artery (LAD) with a left internal mammary artery (LIMA). Loop, F. D., Lytle, B. W., Cosgrove, D. M., et al. "Influence of the Internal Mammary Artery on 10 Years Survival and Other Cardiac Events," *N. Eng. J. Med.,* 1986; 314:1–6. This has encouraged surgeons to extend revascularization with arterial grafts to all coronary arteries. In multiple-vessel disease, other arteries have then to be used, such as: the right internal mammary artery (RIMA), the right gastroepiploic artery, the inferior epigastric artery and the radial artery. At the same time, other techniques are also being used: arterial sequential anastomosis and/or graft elongated and/or Y- or T-grafts. Calafiore, A. M., DiGianmarco, G., Luciani, N., et al. "Composite Arterial Conduits for a Wider Arterial Myocardial Revascularization." *Ann Thorac. Surg.,* 1994:58:185–191 and Tector, A. J., Amundson, S., Schmahl, T. M., et al. "Total Revasculization With T-Grafts". *Ann Thorac. Surg.,* 1994:57:33–39.

Traditionally, bypass graft procedures have required opening the chest wall via a sternotomy, stopping the heart and supporting the patient with a cardiopulmonary bypass system. These requirements are extremely invasive, pose significant risks, require lengthy hospitalization and are expensive. In hope of overcoming these and other problems, physicians have developed a number of alternatives such as percutaneous transluminal coronary angioplasty (PTCA), atherectomy, placement of stents and pharmacological treatments. The most common of these is PTCA which offers relatively short hospitalization periods and is relatively inexpensive. However, these benefits are mitigated by a significant restenosis rate. Similarly, the other alternatives suffer from their own drawbacks.

For these and other reasons, providing an anastomosis between an internal mammary artery and the LAD may be the best therapeutic option for severe proximal lesions. Benetti, F. J., Rizzardi, J. L., Naselli, G., et al., "Anastomosis Manerio Coronaria Sin Circulatión Extracorpórea," *Prense Médica Argentina*, 1985; 73:213. Accordingly, there is a need for improved CABG procedures that simplify surgical techniques and diminish hospital stays and costs.

SUMMARY OF THE INVENTION

The invention comprises a method for performing CABG procedures without the need for opening the chest wall, stopping the heart or providing cardiopulmonary bypass. Generally, at least one small opening is formed in the patient's chest, a target artery for an arterial blood supply is located through an opening in the patient's chest, instruments are introduced through one or more small openings formed in the patient's chest to separate the target artery from its support base; and instruments are introduced through one or more small openings formed in the patient's chest to connect the target artery to a portion of a coronary artery distal from a stenosis in fluid communication therewith to supply arterial blood from the target artery thereto. In a preferred embodiment, a minimal left anterior intercostal thoracotomy provides access to form the anastomosis between the left internal mammary artery (LIMA) and the left anterior descending artery (LAD) while thoracoscopic viewing facilitates harvesting the LIMA. In other embodiments, access to the patient's heart may be obtained through a trocar sheath or other means for providing percutaneous access to the patient's thoracic cavity without opening the chest wall. Depending on the type of access, thoracoscopic visualization is used to locate the arterial blood supply, the location of the coronary artery to be bypassed or the location of the occlusion in the artery. In other embodiments, the diagonal (Dx) or circumflex (Cx) arteries may be bypassed.

BRIEF DESCRIPTION OF THE DRAWINGS

FIGS. 6–10 show the formation of the arteriectomy and the suturing of the LIMA to the LAD to provide an anastomosis.

DETAILED DESCRIPTION OF THE DRAWINGS

In selected cases, it may be possible to avoid the risks of sternotomy and cardiopulmonary bypass, and obtain the benefits of arterial conduits. The patient is intubated with a double-lumen endobronchial tube (not shown) that allows selective ventilation or deflation of the right and left lungs. The left lung is deflated to provide access to the heart and the LIMA. The preferred surgical position of the patient is right lateral decubitus, 30 degrees from horizontal, with the left arm above the head.

Figure 1:
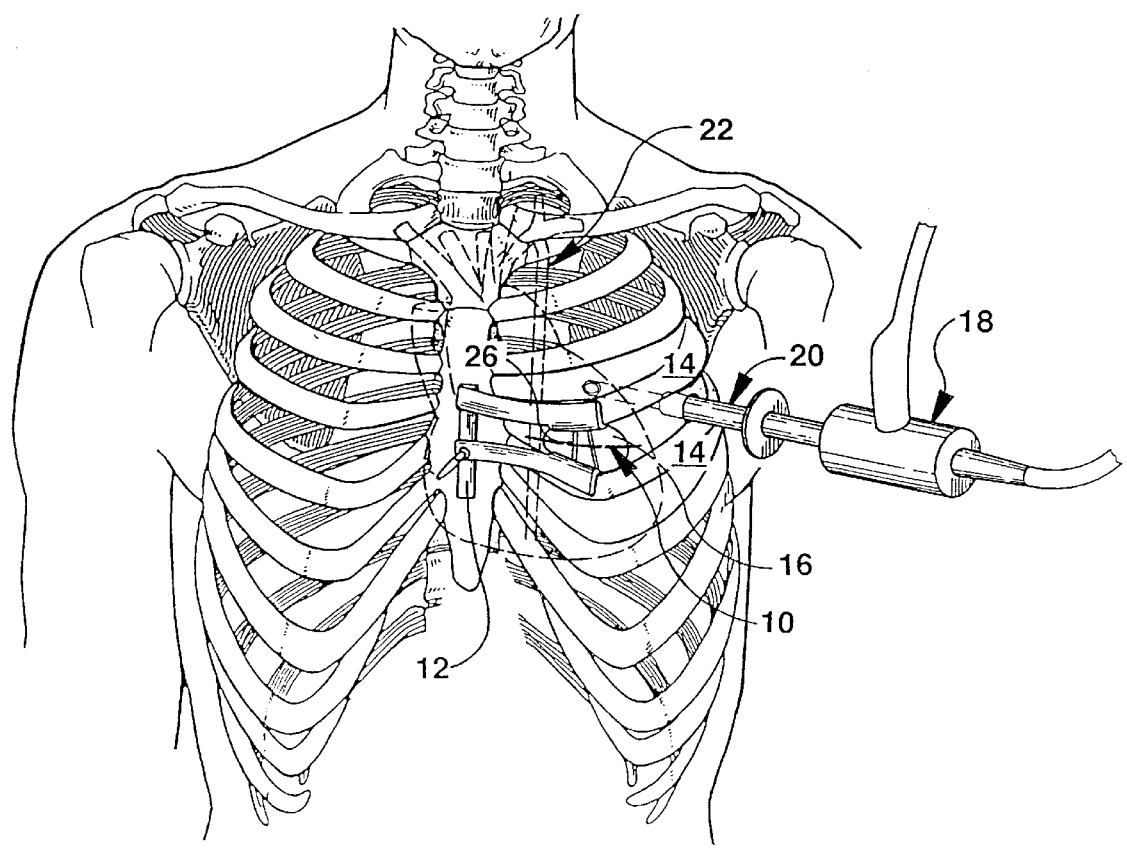
FIG. 1 is a schematic view showing placement of a thoracoscope and formation of a thoracotomy.
Figure 2:
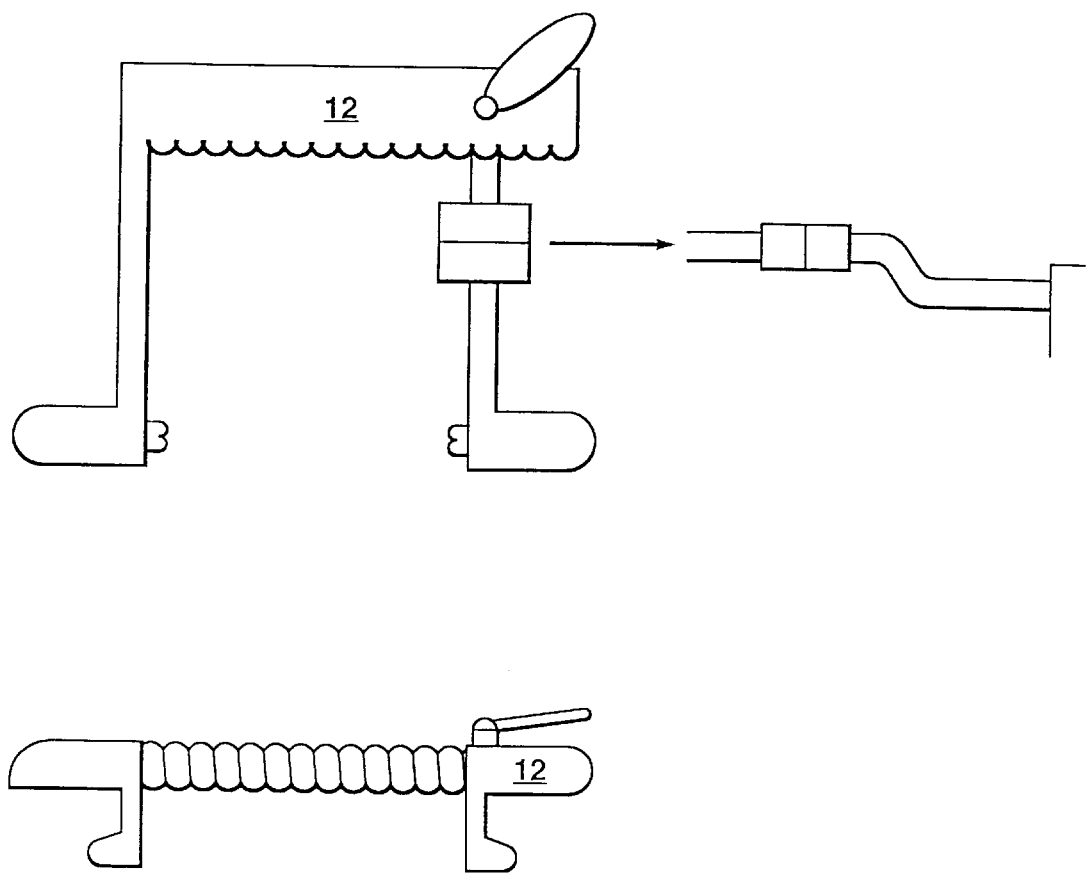
FIG. 2 is an elevational view of a retractor useful in the practice of the invention.
Figure 3:
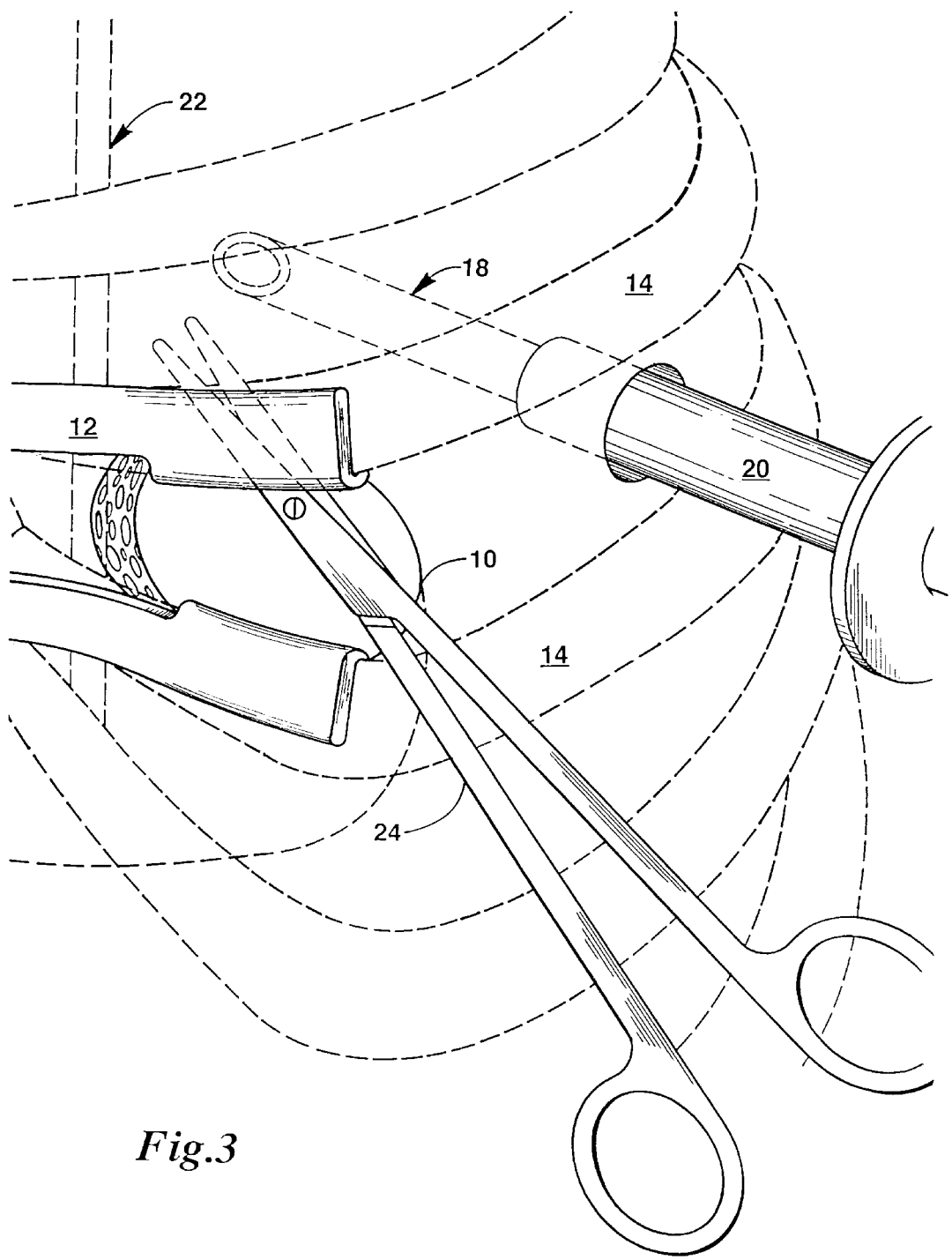
FIG. 3 is a schematic view showing dissection of the LIMA with instruments introduced through the thoracotomy.
Figure 4:
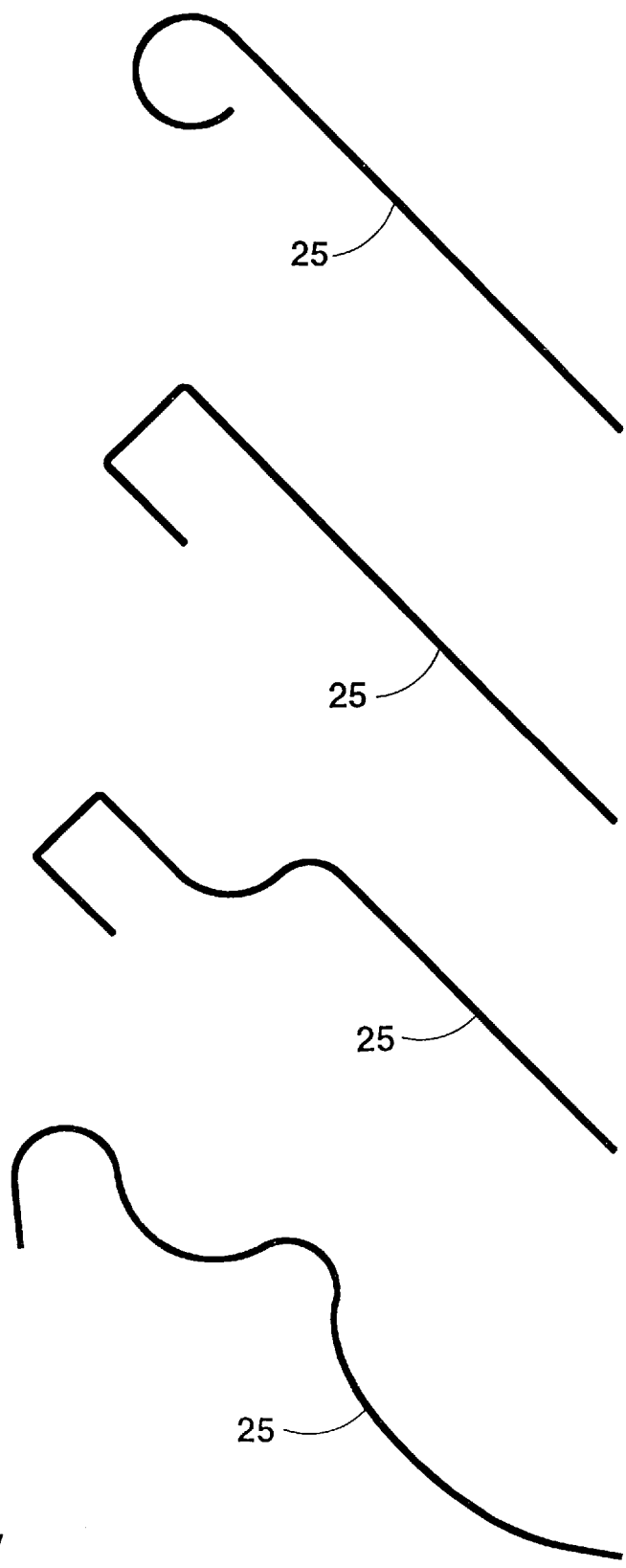
FIG. 4 shows various electrocauteries useful for dissecting the mammary artery.

Referring to FIG. 1, surgery begins with a left anterior thoracotomy 10 over the 4th intercostal space. Other sites are suitable depending on the patient's physiology, particularly the 5th intercostal space. Retractor 12 spreads ribs 14 to provide access to beating heart 16. FIG. 2 shows a special small retractor 12 which can spread the chest both horizontally and vertically. The size of thoracotomy 10 varies depending on the patient, but generally is less than 12 cm. The parietal pleura is dissected and separated from the ribbons, trying to keep it closed, to permit the introduction of thoracoscope 18 through trocar 20 at the 4th intercostal space, medial axillary line. The thoracoscope may be introduced through other areas such as the 5th through 7th intercostal spaces, again depending on the patient's physiology. Thoracoscope 18 is positioned to provide visualization of the LIMA 22. As shown in FIG. 3, instrument 24 is introduced through thoracotomy 10 to dissect LIMA 22. Instrument 24 generally comprises scissors, clip appliers, electrocauteries and other conventional devices useful for the dissection. FIG. 4 shows a variety of electrocauteries 25 useful in the practice of the invention. In some embodiments, it is useful to make a graft with a radial artery coming out from the LIMA in a T-form. This allows the formation of anastomoses with multiple coronary arteries such as sequential grafts to the Dx and Cx arteries.

Following dissection of the LIMA 22, a small pericardial incision is made to expose LAD 26. Access to the LAD and Dx arteries is relatively easy, requiring an incision of about 5 cm. Access to the Cx artery depends on the patient's characteristics and location of the vessels. In some cases, a graft to the Cx artery requires increased rotation of the patent to the right lateral decubitus and some extension of the pericardial incision. Heparin, or other suitable anticoagulant, may be administered to the patient in an appropriate dose such as 1.5 mg/kg.

Figure 5:
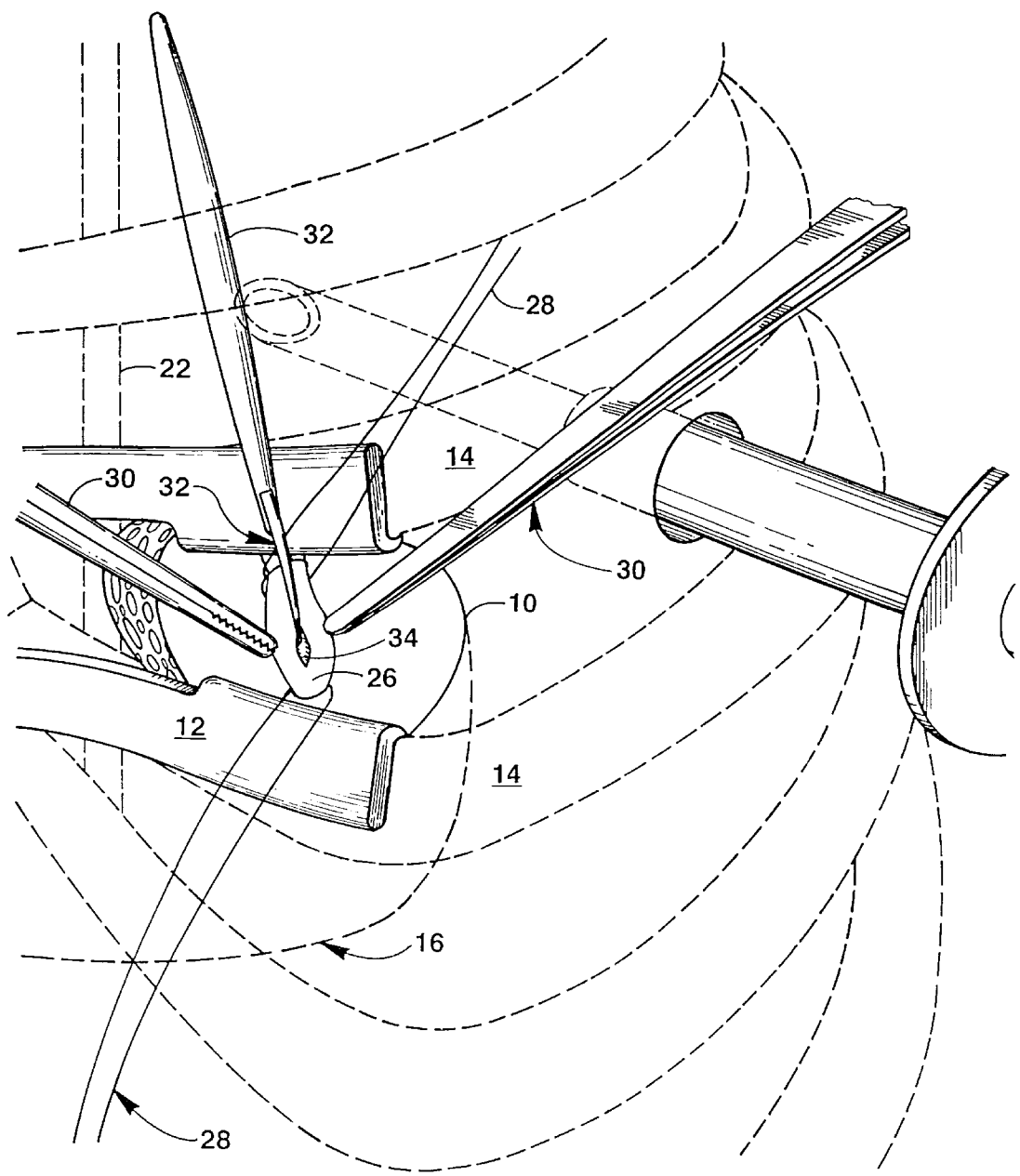
FIG. 5 is a schematic view showing instruments used to make an arteriotomy in the LAD introduced through the thoracotomy.
Figure 9:
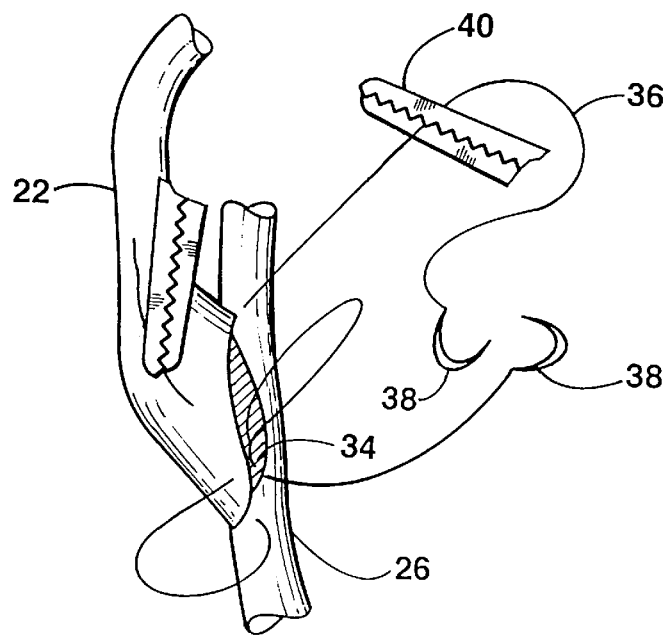
Figure 10:
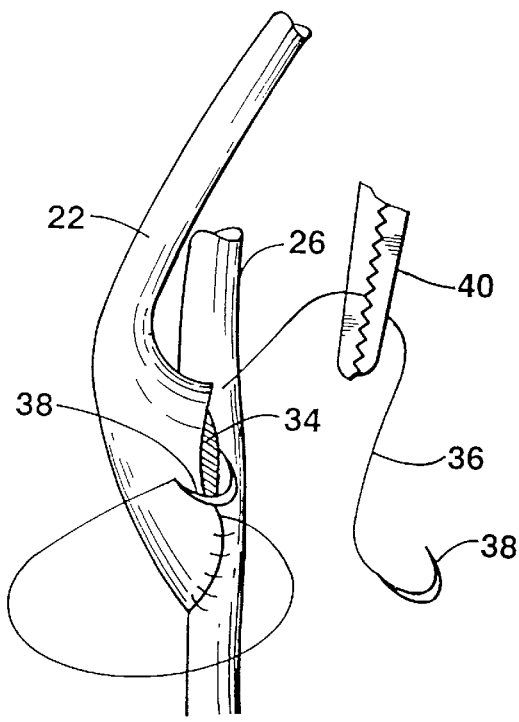

To prevent excess bleeding and to partially stabilize the vessel, a segment of LAD 26 is occluded with ligating stay sutures comprising 2.5 cm lengths of 5/0 polypropylene 28 or other appropriate ligature material as shown in FIG. 5. Applying tension to the ligatures 28 helps stabilize LAD 26 even though heart 16 is beating. Other conventional means for occluding and stabilizing the artery may be suitable. Forceps 30 are introduced through thoracotomy 10 to further stabilize and retract LAD 26. Scalpel 32 is then introduced to form arteriotomy 34 in LAD 26. As shown in FIGS. 6–10, the anastomosis between LIMA 22 and LAD 26 is formed by suturing with 7/0 polypropylene 36 and needle 38 manipulated by forceps 40. Other conventional means may be used as well. Preferably, the anastomosis is formed with a continuous suture and the aid of a conventional blower device (not shown). Further details of the blower are discussed in Tech K. H. T., Panos, A. L., Harmantas, A. A., et al. "Optimal Visualization of Coronary Artery Anastomosis by Gas Jet," *Ann. Thorac. Surg.*, 1991.

Upon completion of the anastomosis, the anticoagulant is reversed by suitable means such as protamine. The hemostasis should be carefully controlled. The thoracotomy is closed in by conventional means; the surgery does not require resection of the costal cartilage. If the pleura is closed, a small tube for drainage may be left in place and removed the same day as surgery. If the pleura is open, a larger tube should be left in place for 24 hours. All drainage tubes are introduced through the small incision for the thoracoscope.

Figure 11:
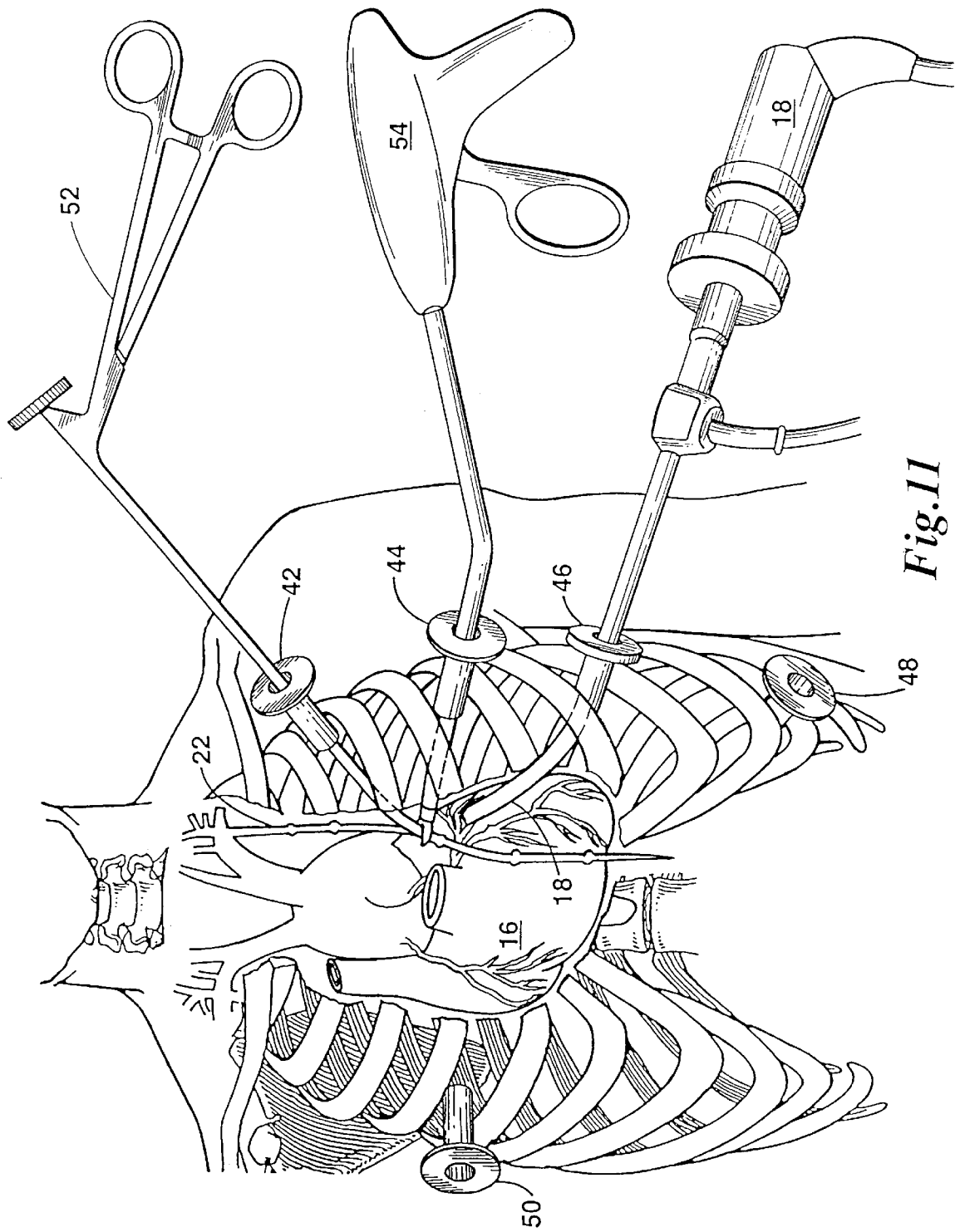
FIG. 11 is a schematic view of instruments for performing the bypass introduced through trocars without a thoracotomy.

FIG. 11 shows a series of trocars 42, 44, 46, 48 and 50 useful in the practice of the invention. In this embodiment, a thoracotomy is not necessary. Instruments 52 and 54 are introduced through the trocars to perform the dissection of the LIMA, the arteriotomy of the LAD and the formation of the anastomosis. Instruments 52 and 54 are conventional and include electrosurgical tools, graspers, forceps, scalpels, electrocauteries, clip appliers, scissors, etc. Although the trocars shown are introduced through the intercostal spaces, other points of access to the thorax may be suitable, such as parasternal punctures, midclavicular line punctures and a subxyphoid puncture.

EXAMPLES

The method of this invention was used to revascularize 10 patients from May to November 1994, one of them being a reoperation (a previous saphenous graft to LAD 11 years before). Sex was male/female in a proportion of 9/1. Age varied from 53 to 74, with an average of 61. Seven patients presented unstable angina, the other 3 suffering from stable angina. Pulmonary function was good in 8 patients, moderate in 1 and severely affected in 1. Four had previous myocardial infarction in other territories.

Access to the heart was through a small thoracotomy over the fifth left intercostal space and a thoracoscope was introduced through the fifth through seventh left intercostal space, medial axillary line, depending on the configuration of the patient's thorax. Eight patients were bypassed with a LIMA graft to LAD, the other two received triple grafts: LIMA to LAD plus a T-graft with radial artery, from the LIMA sequentially to the Dx and Cx arteries.

Mortality, morbidity and perioperative myocardial infarction have been 0%. Six patients were extubated at the operating room. In 5, the pleura was maintained closed. Two patients were discharged from hospital 24 to 36 hours post-surgery; six patients were discharged between 36 and 72 hours; the other 2 were discharged 5 and 6 days post-surgery due to longer recovery time (both were patients with previous acute myocardial infarcts.) No blood transfusions were required. A new coronary angiography was done in 4 patients to monitor the patency of the grafts. Patency of the mammary artery graft was 100% when the patient was restudied before hospital discharge.

The drawings and examples are primarily directed to a graft involving the LIMA and the LAD, the Dx and the Cx arteries; nevertheless, this invention is suitable for many other graft possibilities. For example, other coronary arteries that may be bypassed include the obtuse marginal, the ramus intermedius, the right coronary, the posterior descending and others. Arteries other than the LIMA may be used to provide the arterial blood supply, such as the right internal mammary artery, the gastroepiploic artery and other arteries. Using a free graft shunt using a harvested vein or artery or a synthetic graft to form anastomoses between the aorta and the target coronary artery is also possible. Although intercostal thoracotomies are described to provide access to the heart, in some situations it may be desirable to remove a portion of a rib to improve access. Additionally, the methods of this invention can also be practiced with the use of extracorporeal circulation, making a femoro-femoral cannulation (even percutaneously) to assist the patient for a few minutes during the anastomosis. These and other modifications that would be apparent to one skilled in the art are within the scope of this invention, which is to be limited only by the claims.

What is claimed is:

1. A method for performing a coronary artery bypass graft procedure on the beating heart of a human patient comprising:
    making a small incision in the chest of the patient to access the beating heart;
    maintaining the parietal pleura in a closed condition;
    introducing instruments through said small incision to dissect a target artery having an arterial blood supply;
    stabilizing a coronary artery of said beating heart;
    forming an arteriotomy distal to a stenosis in a coronary artery of said beating heart; and
    bypassing said stenosis in said coronary artery using said arterial blood supply of said target artery to establish blood flow distal to said stenosis.

2. The method of claim 1 wherein said small incision is a minimal thoracotomy.

3. The method of claim 1 wherein the size of said small incision is not substantially greater than 12 cm.

4. The method of claim 1 wherein said coronary artery of said beating heart is stabilized by a method selected from a group consisting of contacting tissue proximate to said coronary artery with forcep means, and tensioning ligatures about said coronary artery.

5. The method of claim 1 wherein said coronary artery of said beating heart is stabilized by forcep means engaging tissue proximate to said coronary artery on either side of said arteriotomy.

6. The method of claim 1 wherein said coronary artery is selected from the group consisting of the left anterior descending, diagonal, circumflex, obtuse marginal, ramus intermedius, right coronary and posterior descending artery.

7. The method of claim 1 wherein said target artery is selected from the group consisting of the gastroepiploic artery, the right internal mammary artery, and the left internal mammary artery.

8. The method of claim 3 wherein said minimal thoracotomy is intercostal and in the left anterior chest, and wherein said target artery is the left internal mammary artery and said coronary artery is selected from the group consisting of the left anterior descending artery, a diagonal artery, and the circumflex artery.

9. The method of claim 1 wherein the formation of said arteriotomy is visualized by a thoracoscope.

10. The method of claim 1 wherein the completion of said anastomosis is visualized by a thoracoscope.

* * * * *